United States Patent [19]

Hlinsky

[11] Patent Number: 5,213,113

[45] Date of Patent: May 25, 1993

[54] DISPOSABLE INTERNAL ELECTRODE WITH STERILIZATION SHIELD AND METHOD OF USING THE SAME

[75] Inventor: Robert L. Hlinsky, Bellevue, Wash.

[73] Assignee: Physio-Control Corporation, Redmond, Wash.

[21] Appl. No.: 824,034

[22] Filed: Jan. 22, 1992

[51] Int. Cl.⁵ .............................................. A61N 1/00
[52] U.S. Cl. ................... 128/800; 128/783; 128/419 D; 128/642
[58] Field of Search .................. 128/419 D, 800, 801, 128/784, 783; 439/346, 324, 332, 233, 338; 403/348, 349; 606/42

[56] References Cited

U.S. PATENT DOCUMENTS

| | | | |
|---|---|---|---|
| 3,224,447 | 12/1965 | Becker et al. | 128/421 |
| 3,353,664 | 11/1967 | Armentrout et al. | 206/461 |
| 3,389,703 | 6/1968 | Criswell et al. | 128/404 |
| 3,826,245 | 7/1974 | Funfstuck | 128/2.06 |
| 3,946,743 | 3/1976 | Milani et al. | 128/404 |
| 3,961,623 | 6/1976 | Milani et al. | 128/2.06 |
| 4,108,161 | 8/1978 | Samuels et al. | 206/363 X |
| 4,351,330 | 9/1982 | Scarberry | 128/419 D X |
| 4,359,052 | 11/1982 | Staub | 606/30 |
| 4,921,096 | 5/1990 | McFarlane | 206/363 X |
| 5,052,849 | 10/1991 | Zwart | 403/349 X |

Primary Examiner—Lee S. Cohen
Assistant Examiner—Samuel Gilbert
Attorney, Agent, or Firm—Christensen, O'Connor, Johnson & Kindness

[57] ABSTRACT

An internal defibrillation electrode (10) is disclosed including a disposable electrode (12) and a reusable handle (14). The electrode includes an electrode spoon (16), a shaft (18), and a barrier sleeve (20). The handle includes a handle body (58), electrical cable (60), sleeve connector (62), and electrical connector (64). The handle has a dagger-style configuration that makes the electrode assembly easy to use and is further constructed to allow the electrode to be quickly and reliably attached. In that regard, during assembly, a bayonet (32) on the shaft of the electrode is engaged in a bayonet receptacle (68) of the handle. The sleeve is then pulled over the handle to form a barrier between the handle and the environment. After the electrode assembly is used, the sleeve is removed from the handle, the electrode disengaged from the handle, and the electrode disposed of. After attaching a new electrode, the handle is then ready for immediate service. The handle can also be used with a reusable electrode that does not include a barrier sleeve. To that end, the handle is constructed to exhibit a relatively long life when subjected to repeated steam sterilization.

17 Claims, 8 Drawing Sheets

DISPOSABLE INTERNAL ELECTRODE WITH STERILIZATION SHIELD AND METHOD OF USING THE SAME

TECHNICAL AREA

The present invention relates in general to defibrillation and, more particularly, to disposable electrode assemblies for internal defibrillation.

BACKGROUND OF THE INVENTION

Electrical impulses are sometimes applied to a patient's heart to terminate irregularities in the heart's operation. For example, defibrillation involves the discharge of an electrical impulse to a patient's heart to terminate a potentially fatal form of arrhythmia known as ventricular fibrillation. Less severe forms of arrhythmia can often be electrically terminated by a process referred to as synchronized cardioversion. For the purpose of the ensuing discussion, however, such processes involving the application of electrical energy to a patient will be collectively referred to as defibrillation.

The source of the electrical impulses used to terminate arrhythmic operation of the heart is a device known as a defibrillator. The defibrillator is electrically connected to the patient by a pair of cables and electrode assemblies. Typically, each assembly includes a handle, an electrode that provides the requisite electrical contact with the patient, and a discharge button for controlling the discharge of energy through the electrode to the patient.

The electrode assemblies are usually designed for either external or internal use. As will be appreciated, external electrode assemblies are employed noninvasively, with the electrodes positioned on the patient's chest. In contrast, internal electrode assemblies are employed during surgery and include electrodes that are applied directly to the patient's heart.

A conventional internal electrode assembly includes a handle and a permanently attached electrode. The handle, which is held like the handle of a pan, includes a discharge switch adjacent the end the electrode is attached to. This "pan handle" configuration, unfortunately, makes the assembly somewhat awkward to use in an opened chest cavity.

Because internal electrode assemblies are placed in contact with the heart, the internal assemblies must be sterile. Internal assemblies have traditionally been intended for reuse and must be sterilized after each use.

In that regard, although the assembly could be relatively quickly sterilized with steam, the handle of a conventional electrode assembly does not protect electrical components, such as the discharge switch, sufficiently to allow the handle to be steam sterilized. Thus, time-consuming ethylene oxide (ETO) sterilization processes are used for the entire assembly. If only a single pair of electrode assemblies are purchased for a defibrillator, the defibrillator cannot be used to perform internal defibrillation during those periods in which the assemblies are being sterilized. While this problem can be overcome by purchasing a supply of reusable assemblies for each defibrillator, system expense may increase significantly.

Alternatively, disposable electrode assemblies have been developed that are less expensive than conventional reusable assemblies. Still, a disposable assembly generally includes an electrode, handle, discharge button, cable, and connector. As a result, a single-use disposable electrode assembly is not particularly economical to use either.

As will be appreciated from the preceding remarks, it would be desirable to provide an internal electrode assembly that can be quickly sterilized. It would also be desirable to provide an internal electrode assembly that is simple and reliable in construction, as well as convenient to hold and use.

SUMMARY OF THE INVENTION

A disposable internal electrode is disclosed for use in effectively sterilizing a reusable handle. In accordance with a particular aspect of the invention, the electrode is for use by an operator with a handle to couple a patient to a medical instrument. The electrode includes an electrode element and a barrier. The electrode element is attachable to the handle and is for contacting the patient. The barrier is for providing a barrier between the handle and the patient.

In that regard, the electrode element may include a spoon and a shaft, having first and second ends, with the first end of the shaft being attached to the spoon. The barrier is a tubular sleeve having first and second ends with the first end being coupled to the shaft. The entire electrode may be contained in a package including a first compartment for receiving the spoon and the sleeve and a second compartment for receiving the second end of the shaft.

BRIEF DESCRIPTION OF THE DRAWINGS

The invention will presently be described in greater detail, by way of example, with reference to the accompanying drawings, wherein.

DETAILED DESCRIPTION OF THE PREFERRED EMBODIMENT

Figure 1:
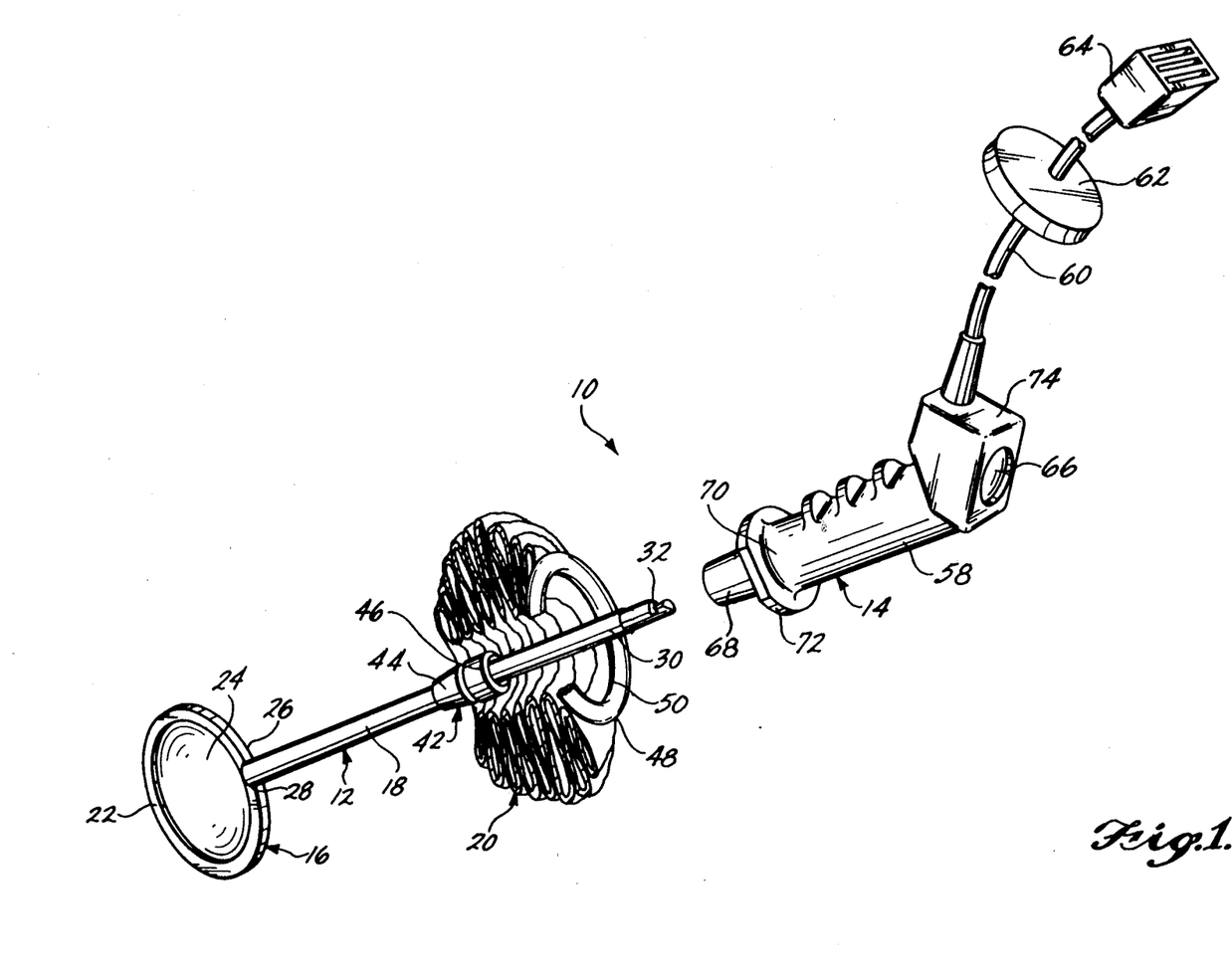
FIG. 1 is partially exploded illustration of a first embodiment of a defibrillation electrode assembly, including a disposable electrode and a reusable handle, constructed in accordance with the present invention.

Referring now to FIG. 1, an internal defibrillation electrode assembly 10 is shown. Assembly 10 is one of two such electrode assemblies used with a defibrillator (not shown) to apply electrical energy to a patient and stimulate the proper operation of the patient's heart. As will be described in greater detail below, each electrode assembly 10 includes a disposable electrode 12 and a reusable handle 14.

The handle 14 is electrically and mechanically connected to the defibrillator and allows an operator to securely and comfortably grasp and position the electrode assembly 10, as well as control the discharge of electrical energy from the defibrillator to the patient. The electrode 12 can be electrically and mechanically connected to the handle 14 quickly and securely and allows an electrical connection to be made between assembly 10 and the patient's heart.

As described more fully below, the disposable electrode 12 and reusable handle 14 are each constructed to address the problem of internal electrode assembly sterilization, albeit in different fashions. In that regard, the disposable electrode 12 is designed to "effectively sterilize" the handle 14 by providing a sterile barrier between the patient and handle 14. Alternatively, the reusable handle 14 is designed to exhibit a long life when sterilized with conventional processes, allowing it to be used with more conventional reusable electrodes.

Addressing the two main components of electrode assembly 10 in greater detail, the electrode 12 includes an electrode spoon 16, an electrode shaft 18, and a barrier sheath or sleeve 20. The electrode spoon 16 is a generally circular disc of electrically conductive material and includes a back surface 22 and a discharge surface 24. The discharge surface 24 is concave to roughly conform to the surface of the heart. As a result, a substantial portion of the discharge surface 24 can be easily maintained in contact with the heart, reducing the resistance of the spoon/heart interface and ensuring the efficient transfer of energy to the heart.

The back surface 22 of the electrode spoon 16 is convex. In addition, the back surface 22 is covered with an insulative material 26 to confine the transfer of electrical energy between the spoon 16 and the patient to the discharge surface 24. The insulative material 26 may be any biologically suitable dielectric material such as a one millimeter thick layer of polypropylene.

The shaft 18 of electrode 12 includes a spoon end 28 and handle end 30. The spoon end 28 of shaft 18 is connected to the electrode spoon 16, with the shaft 18 extending radially from the edge of spoon 16. The handle end 30 of shaft 18 is provided with an approximately one-quarter turn bayonet 32, which allows shaft 18 to be electrically and mechanically coupled to the handle 14, as described in greater detail below.

The electrode shaft 18 is made of the same electrically conductive material as spoon 16. With the exception of the bayonet 32, the surface of shaft 18 is covered with the same insulative material 26 as the back surface 22 of spoon 16. Thus, electrical energy transferred to the shaft 18 via the bayonet 32 is generally confined to shaft 18 until it reaches the electrode spoon 16, where it can be transferred to the patient through the discharge surface 24.

Figure 2:
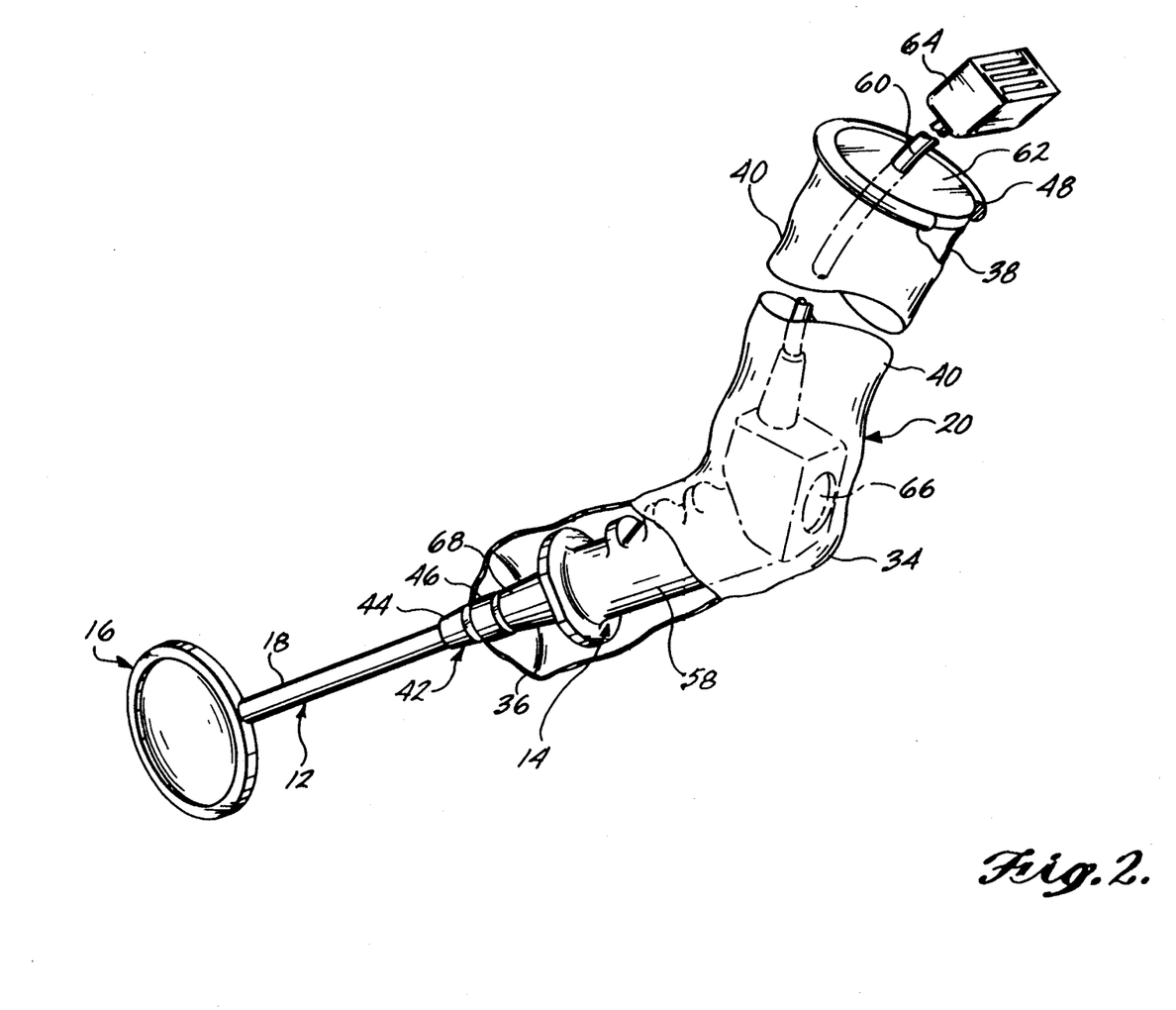
FIG. 2 is an illustration of the electrode assembly of FIG. 1, assembled for use.

Addressing now the barrier sleeve 20 of electrode 12, sleeve 20 is a generally tubular, fluid-impermeable membrane. As shown in FIG. 2, sleeve 20 includes a body 34, a tapered electrode end 36, and a handle end 38. As will be described in connection with FIG. 2 below, sleeve 20 is included to effectively sterilize handle 14 by providing a barrier between a substantial portion of the handle 14 and the patient.

Sleeve 20 is made from, for example, an elastic material such as latex. The sleeve 20 is generally cylindrical and may have a thickness of on the order of 0.8–1.3 millimeters, a main diameter of roughly 2.5–3.8 centimeters, and a length of roughly one meter. The body 34 of sleeve 20 is provided with a plurality of longitudinally spaced-apart, circumferential pleats 40, which allow the sleeve 20 to be longitudinally collapsed and extended more easily.

Figure 3:
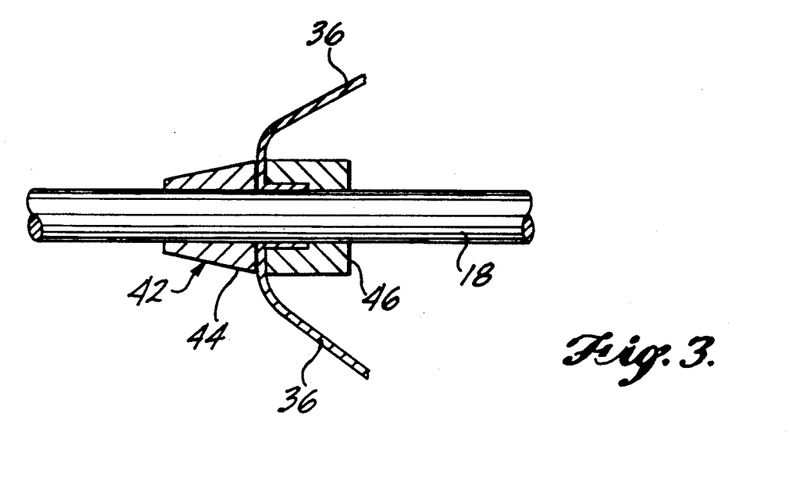
FIG. 3 is a partial sectional view of the connection between two components of the electrode of FIG. 1, a barrier sleeve and electrode shaft.

At the electrode end 36 of sleeve 20, an electrode/sleeve connector 42 is included to provide a sealed connection between the barrier sleeve 20 and the electrode shaft 18, roughly halfway between the spoon and handle ends 28 and 30 of shaft 18. In that regard, as shown in greater detail in the cross-sectional view of FIG. 3, connector 42 includes a tapered collar 44 and a cylindrical collar 46. Collar 44 is generally intended to be positioned on shaft 18 outside the sleeve 20. The collar 46 is generally intended to be positioned on shaft 18, adjacent collar 44 but inside the sleeve 20, and includes a stepped edge that receives the electrode end 36 of sleeve 20. The sleeve 20 is thus secured between collars 44 and 46, as well as sealed to shaft 18 by collar 46. Collars 44 and 46 are made, for example, of polypropylene or latex and are positioned coaxially about the shaft 18.

The handle end 38 of sleeve 20 is also provided with a connector 48. The connector 48 is generally ring-shaped, having a diameter roughly equivalent to that of sleeve 20. The connector 48 includes an internal, convex contoured surface 50, described in greater detail below, for engaging a component of the handle 14.

Figure 4:
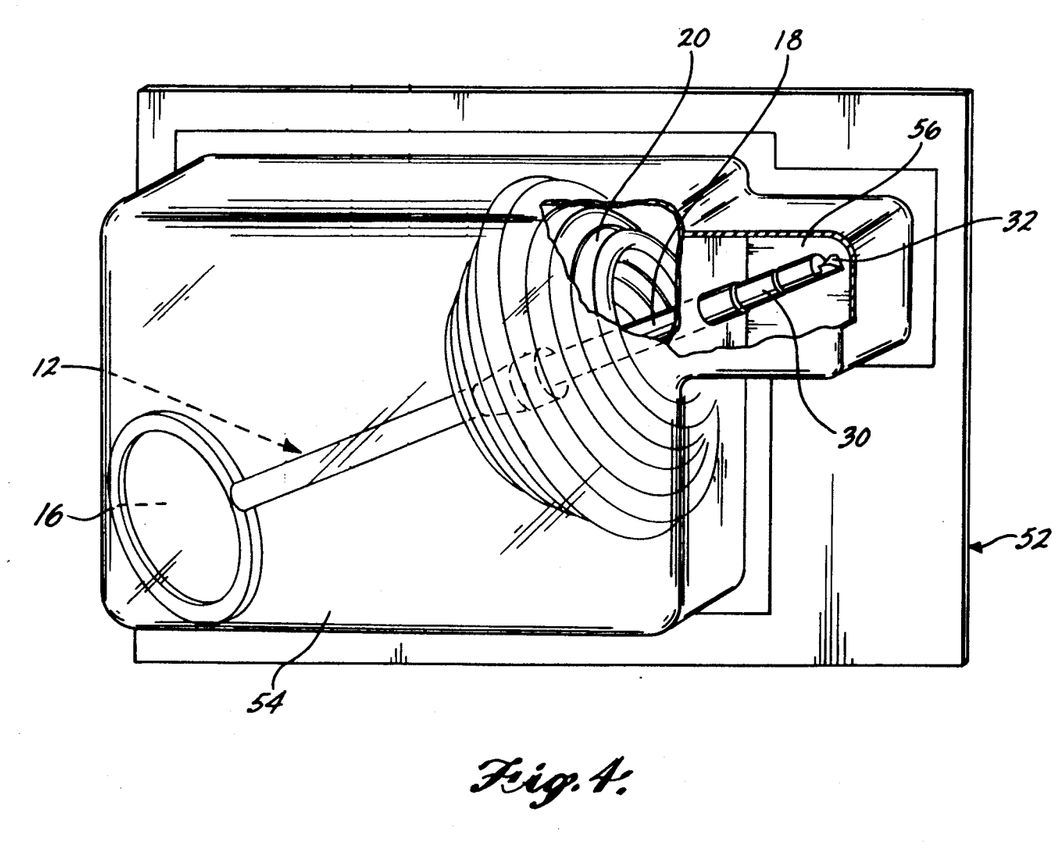
FIG. 4 is an illustration of the packaging used to ensure that the disposable electrode remains sterile prior to use.

The disposable electrode 12 described above is preferably packaged in a double-barrier sterile package 52, shown in FIG. 4. In that regard, with the sleeve 20 collapsed about the shaft 18 of electrode 12 in the manner generally shown in FIG. 1, the sterile electrode spoon 16 and sleeve 20 are sealed within a first compartment 54 of package 52. The shaft 18 of electrode 12 projects from this compartment 54. The projecting handle end 30 and bayonet 32 of shaft 18 are, however, received within a second compartment 56 of package 52.

In this manner, the double-barrier sterile package 52 contains the entire disposable electrode 12. As a result, electrode 12 is generally easier to store and distribute and is also physically protected and kept sterile. The double-barrier design of package 52 further allows the spoon 16 and sleeve 20 to remain protected in compartment 54 when the bayonet 32 is exposed and connected to handle 14, as described in greater detail below.

As will be appreciated, the two-compartment, double-barrier package 52 can be constructed in various manners. For example, the package 52 may employ a single-layer exterior, with a wall included to divide the package 52 into compartments 54 and 56. Alternatively, compartments 54 and 56 may be formed by two nested packages that collectively form package 52.

Figure 5:
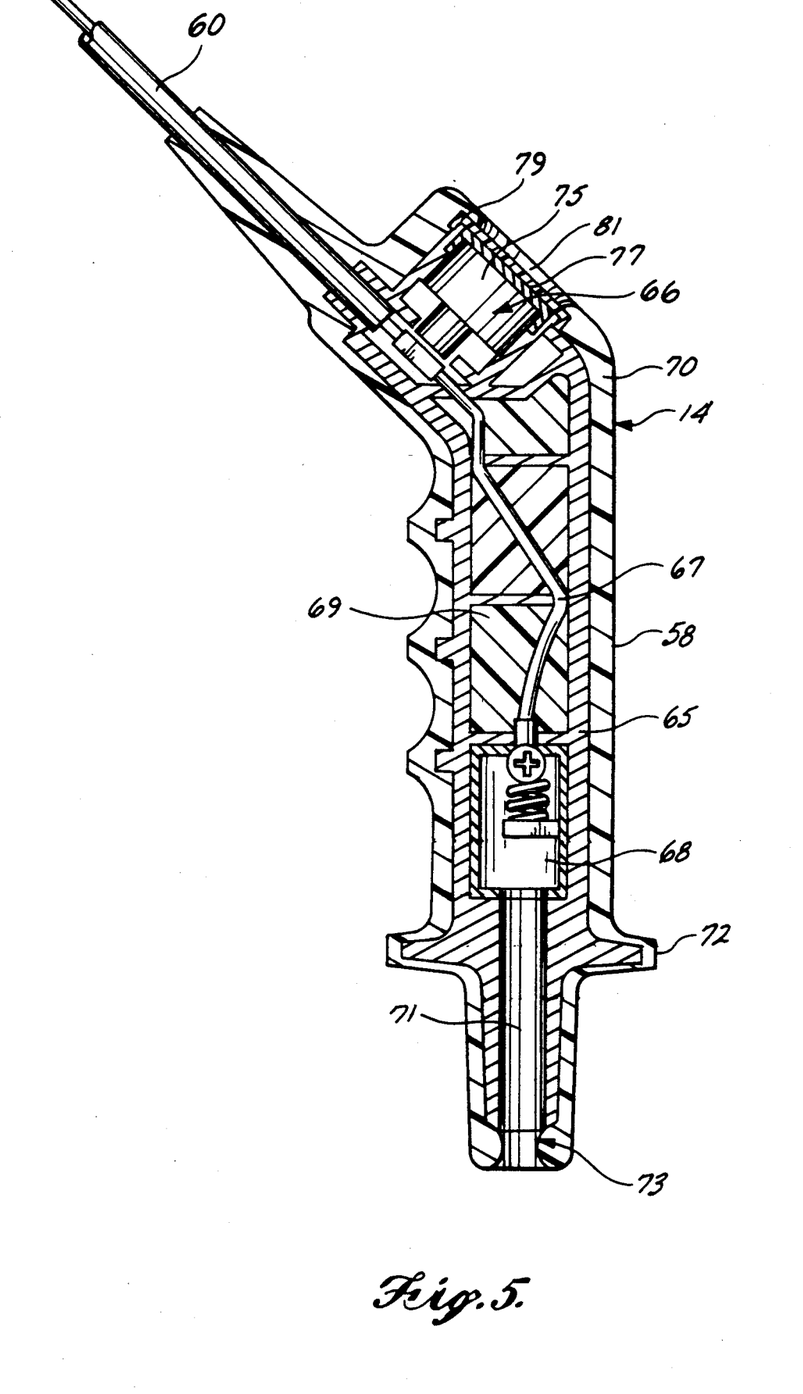
FIG. 5 is a sectional view of a portion of the handle of FIG. 1.

Addressing now the construction of the handle 14 of assembly 10, reference is had to FIGS. 1 and 5. As shown, handle 14 includes a handle body 58, electrical cable 60, barrier connector 62, and electrical connector 64. Addressing these components individually, the body 58 has "pistol-grip" design, including finger ridges that cooperatively position the user's fingers and enhance the user's grip on handle body 58. The handle body 58 includes a frame 65 that is employed to support a discharge switch assembly 66, bayonet receptacle 68, and power wire 67, which couples the bayonet receptacle 68 and discharge switch assembly 66 in series with the electrical cable 60.

The handle body 58 is formed by a multiple-step process in which the components of the handle body 58 are first positioned in various recesses and slots provided in the frame 65. The portion of the frame 65 that receives the switch assembly 66 is then covered with an encapsulant 69, such as epoxy, to protect assembly 66. Next, the entire frame is encapsulated within a molded plastic cover 70, which fills the remaining recesses of frame 65 and gives the handle body 58 its general shape.

This multiple-layer construction process produces a handle 14 that is more resistant to the rigors of steam sterilization than conventional electrode assembly handles. As will be appreciated, this feature is of relatively little importance when handle 14 is used with disposable electrode 12 because electrode 12 effectively sterilizes the handle 14 without resort to, for example, steam sterilization. On the other hand, if handle 14 is used with a reusable electrode, as described in greater detail below, the whole assembly 10 can be steam sterilized. The encapsulant 69 and cover 70 then provide two independent layers of protection for the switch assembly 66 and power wire 67, allowing these components to be largely unaffected by the sterilization process. As a result, the reusable handle 14 may exhibit a relatively long life.

Addressing the next component of handle body 58, as shown in FIG. 5, the bayonet receptacle 68 is located adjacent a first end 72 of the handle body 58. The bayonet receptacle 68 is designed to receive and securely engage the bayonet 32 provided on the handle end 30 of the electrode shaft 18, in a manner described in greater detail below.

The bayonet receptacle 68 opens to the exterior of handle body 58 via a cylindrical passage 71 provided in the handle frame 65 and cover 70. Passage 71 is generally of sufficient length and diameter to receive the shaft 18 of the electrode assembly 12. Preferably, some clearance is provided between the passage 71 and shaft 18, however, to prevent a similarly dimensioned shaft, without the requisite bayonet 32, from being frictionally retained in the passage 71.

If additional support for the shaft 18 is desired, a blood seal 73 can be included at the open end of passageway 71, as a molded feature of cover 70. The blood seal 73 has a circular, convex inner surface that provides an interference fit with respect to shaft 18. Given the resilient nature of the cover material, the shaft 18 can still be inserted but is wiped clean by the blood seal 73. The seal 73 also provides a largely fluid-tight seal against shaft 18.

Figure 6:
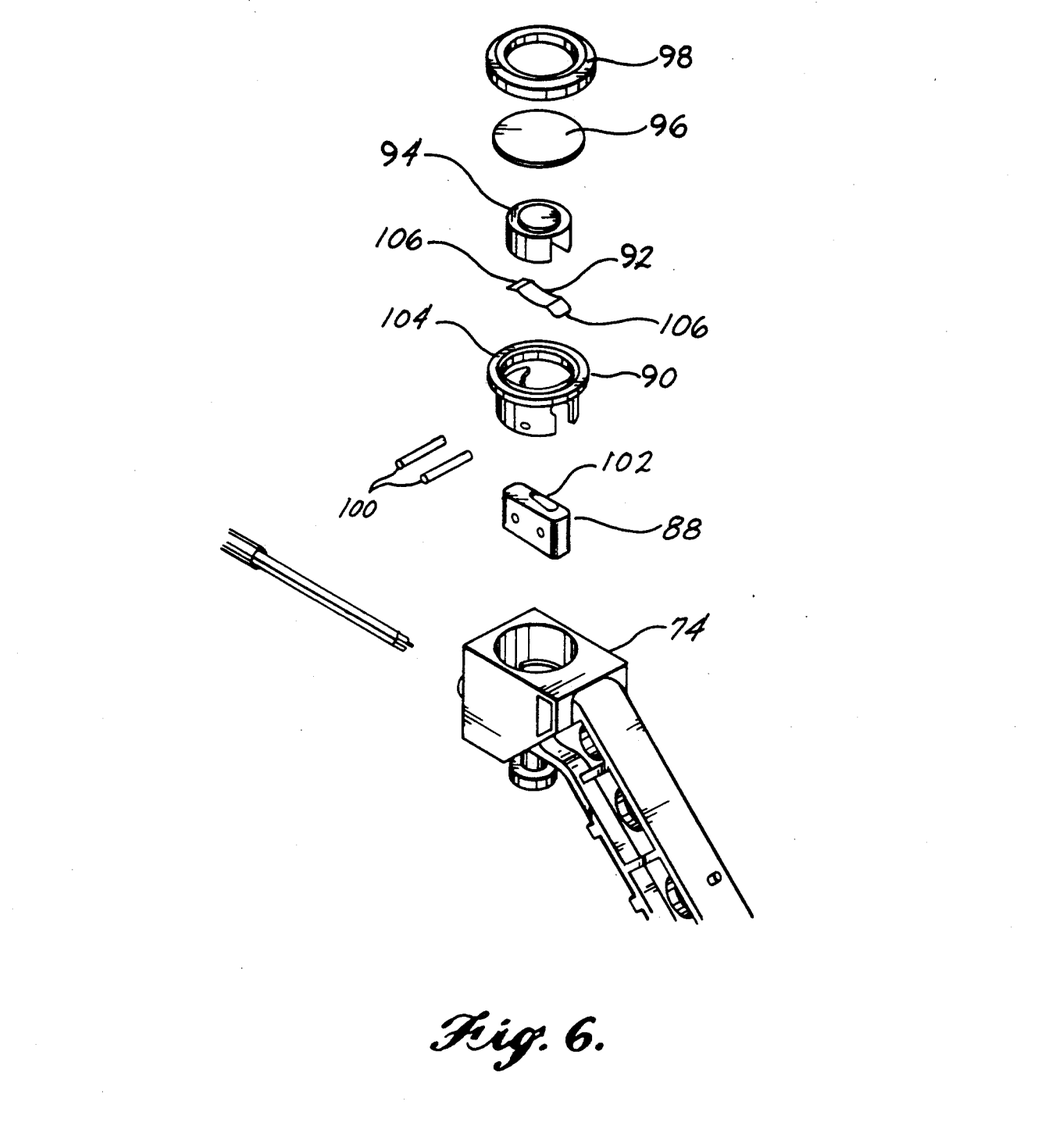
FIG. 6 is a partial exploded view of the handle of FIG. 1.

As shown in FIG. 6, the discharge switch assembly 66 included on handle body 58 has several different components: a microswitch 88, housing 90, tactile device 92, pushbutton cap 94, pushbutton sealing membrane 96, locking ring 98, and retaining pins 100. The microswitch 88 is a hermetically sealed device, including a pair of normally open contacts that are connected in series with the power wire 67 and electrical cable 60. The microswitch 88 is actuated by a switch arm 102.

As noted, the assembly 66 also includes a roughly cylindrical housing 90, which supports the microswitch relative to the frame 65 of handle body 58. In that regard, the microswitch is received within the cylindrical housing and both items are fixed relative to frame 65 by pins 100 extending therethrough. The upper edge of the cylindrical housing 90, adjacent the switch arm 102, is provided with a groove 104 that is included to support tactile device 92.

Tactile device 92 prevents the unintentional actuation of the microswitch 88 and provides the user with a clear tactile sense that microswitch 88 has been actuated. In that regard, unless microswitch 88 is custom designed, the force and/or switch arm displacement required to actuate microswitch 88 may not be enough to prevent the microswitch 88 from being accidentally actuated by the user when the pushbutton sealing membrane 96 is touched. The tactile device 92 is included to effectively alter these characteristics of microswitch 88.

In a currently preferred arrangement, the tactile device 92 is a leaf spring, positioned between the actuator arm 102 of microswitch 88 and the pushbutton cap 94. As noted above, the two ends 106 of leaf spring 92 may be supported by a groove 104 on the cylindrical switch housing 90. When positioned in this manner, a force applied to the pushbutton sealing membrane 96 must overcome the resistance of the leaf spring to close the microswitch's contacts. The leaf spring 92, thus, gives microswitch 88 a spring-loaded, over-the-center, snap action and a more pronounced tactile operation.

As previously noted, actuation forces are applied to leaf spring 92 and microswitch 88 via the pushbutton sealing membrane 96 and cap 94. The pushbutton cap 94 is a roughly cylindrical stainless steel element that is received within housing 90 and covers tactile device 92 and microswitch 88. The relatively thin plastic membrane 96 is placed over the cap and is retained in a circular opening 81 in the handle cover 70 by the locking ring 98, which may be molded in place.

The discharge switch assembly 66 described above is located at the second end 74 of handle body 58, adjacent the junction of the electrical cable 60 and handle body 58. In that regard, the second end 74 of handle body 58 is aligned at an angle of roughly 135 degrees with respect to the first end 72 of handle body 58.

When the user grasps handle body 58, the user's thumb is positioned over the pushbutton membrane 96, at a natural angle. Further, because the internal electrode 12 projects from the end 72 of handle body 58 opposite switch assembly 66, the electrode assembly 10 is held in a manner similar to that in which a dagger might be held. This "dagger-style" configuration allows the electrode assembly to be comfortably held and the electrode spoon 16 securely positioned on a patient's heart. In contrast, conventional internal defibrillation electrode assemblies include a discharge switch positioned adjacent the electrode end of the handle, requiring the handle to be held like the handle of a pan. Such conventional designs are awkward to hold and require more effort to securely position the electrode spoon on the patient's heart.

The electrical cable 60 extends from the handle body 58 at a strain relief, provided as part of the molded handle cover 70, and terminates at an electrical connector 64. The connector 64 is constructed to provide the requisite electrical/mechanical connection with a mating connector provided on the defibrillator. With connector 64 attached to the mating connector, cable 60 then electrically connects the components of handle 14 to the defibrillator.

Figure 7:
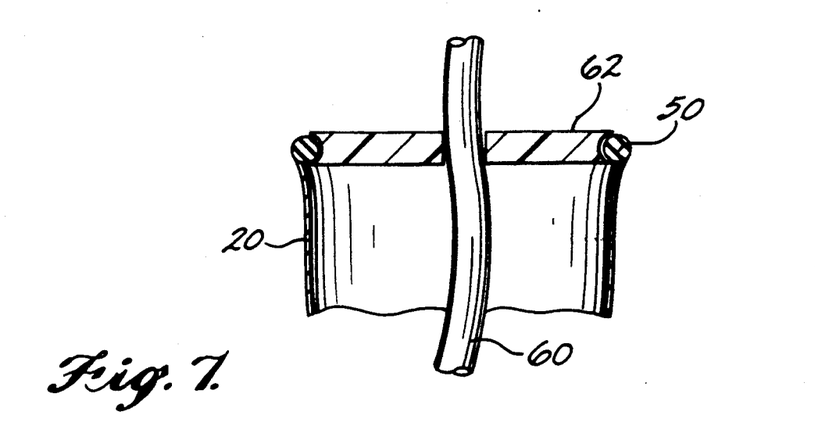
FIG. 7 is a sectional view of the connection between the barrier sleeve of the electrode and a cable, included as part of the handle.

As noted above, the handle 14 also includes a barrier connector 62. The barrier connector 62 is preferably positioned on cable 60 roughly one meter from the handle body 58 and may be adhered thereto or formed integrally therewith. Connector 62 is a substantially disk-shaped piece constructed to cooperatively engage the connector 48 provided on sleeve 20. More particularly, as shown in FIGS. 1 and 7, the perimeter of connector 62 includes a contoured concave surface 76 that receives the mating convex surface 50 of connector 48 with a positive or snap fit. As a result, the sleeve 20 is effectively sealed to the cable 60, providing a barrier between the covered portion of the cable 60 and the environment.

Although the construction of the electrode 12 and handle 14 described above is preferred, as will be appreciated, various other constructions can be successfully employed. In that regard, the spoon 16 and shaft 18 of electrode assembly 12 can be altered without sacrificing the benefits of the invention. Similarly, the components of handle 14 can be varied as desired. Even the barrier sleeve 20 can be altered, for example, in shape, size, and material, as well as the manner and point of connection to the remaining components of electrode 12 and handle 14.

Having reviewed the construction of the various components of electrode assembly 10, the construction and operation of assembly 10 will now be described. In that regard, a disposable electrode 12, stored in a double-barrier sterile package 52, is first prepared for connection to the reusable handle 14 in the following manner. The package 52 is torn open at a marked corner, exposing the bayonet 32 provided on the handle end 30 of electrode shaft 18. Next, the protruding handle end 30 of shaft 18 is grasped by the user and the bayonet 32 is inserted into the bayonet receptacle 68 of the handle body 58. The electrode 12 is then rotated with respect to the handle body 58 to lock electrode 12 in place.

Discussing the connection of the electrode shaft bayonet 32 to bayonet receptacle 68 in greater detail, reference is had to FIGS. 8A through 8D. The bayonet 32 includes a spring-bearing surface 83 and initial alignment surface 85, joined by a cam surface 87. As will become apparent from the ensuing discussion, this cammed construction is designed to accommodate dimensional differences and tolerances in the bayonet 32 and receptacle 68.

The spring-bearing surface 83 of bayonet 32 is substantially perpendicular to the axis of shaft 18, while alignment surface 85 is parallel to, but offset from, the shaft's axis. A first notch 89 extends from a portion of the initial alignment surface 85 to a wider second notch 91 having a locked alignment surface 93. Alignment surface 93 is spaced on the opposite side of the shaft's axis from surface 85 and defines an acute angle with respect to surface 85.

Figures 8A, 8B, 8C:
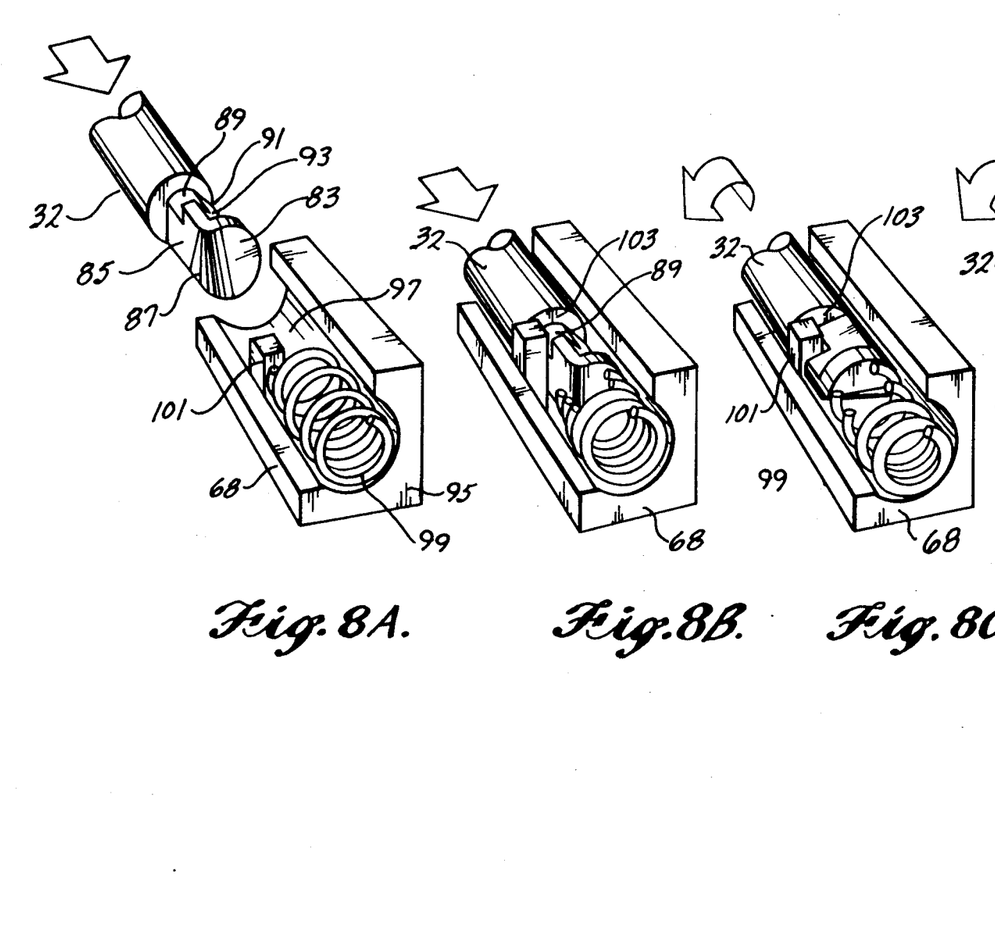
FIGS. 8A through 8D illustrate the manner in which the electrode and handle of FIG. 1 are electrically and mechanically connected.

The bayonet receptacle 68, in turn, includes a housing 95 provided with a cylindrical passage 97. A bias coil spring 99 is coaxially received within passage 97. Spring 99 is retained in position by a locking pin 101 extending transversely through passage 97.

To lock the bayonet 32 in the bayonet receptacle 68, the bayonet 32 is first inserted into the receptacle passage 97 as shown in FIGS. 8A and 8B. In FIG. 8A, surface 85 of bayonet 32 is aligned with the locking pin 101 prior to insertion. As a result, the bayonet 32 clears the locking pin 101, allowing the spring-bearing surface 83 to contact spring 99.

If the electrode shaft 18 is not oriented in the manner shown in FIG. 8A upon insertion, the spring-bearing surface 83 will initially abut the locking pin 101, restricting further insertion of bayonet 32 into the receptacle passage 97. By rotating shaft 18, however, the cam surface 87 will be brought into contact with locking pin 101 and will bring the alignment surface 85 into contact with locking pin 101 upon further rotation. At this point, the bayonet 32 can be inserted into passage 97 sufficiently to compress the spring 99 as shown in FIG. 8B.

Eventually, insertion of the bayonet 32 into passage 97 is restricted by a lip 103, defined between the bayonet 32 and the handle end 30 of shaft 18. The compression of spring 99 may also inhibit the insertion of bayonet 32. At this point, the first notch 89 is aligned with the locking pin 101, as shown in FIG. 8B. The width of notch 89 is slightly greater than that of locking pin 101, allowing the shaft 18 to be rotated counterclockwise, as shown in FIG. 8C.

Figure 8D:
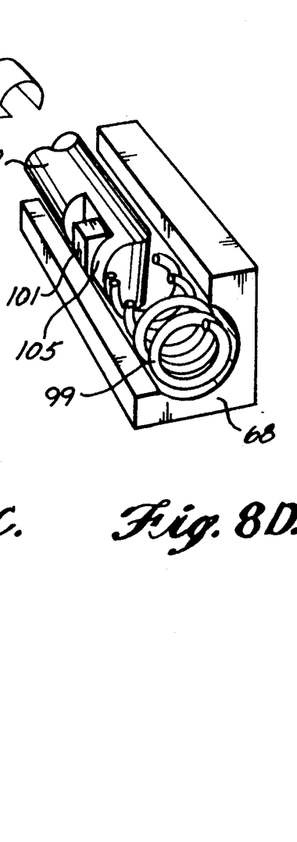

If shaft 18 is rotated approximately 90 degrees, the locking pin 101 clears the first notch 89 and is positioned entirely in the wide second notch 91. At this point, the locking pin 101 is adjacent a first lip 103 on bayonet 32. If the electrode shaft 18 is released, however, the force of spring 99 against the bearing surface 83 of bayonet 32 will securely force a second bayonet lip 105 against the locking pin 101, as shown in FIG. 8D. Lip 105 is located between the bearing surface 83 and second notch 91 of bayonet 32. In this manner, the bayonet 32 is mechanically locked in place and a good electrical connection between the electrode shaft 18 and conductive housing 95 of the bayonet receptacle 68 is established.

The mating surfaces of lip 105 and locking pin 101 are shown substantially perpendicular to the axis of shaft 18 and passage 97 in FIG. 8D. They can, however, be offset at an angle with respect to the axis of shaft 18 and passage 97 to more securely lock the electrode in place. With the surfaces angled, the spring 99 must be compressed and the shaft 18 rotated to disengage the surfaces. The bayonet 32 is then withdrawn by reversing the steps described above.

The secure engagement of bayonet 32 by receptacle 68 is further assisted by the relative dimensioning of the two components. In that regard, the bayonet 32, when viewed on end, has a perimeter that defines more than one half of a circle whose diameter corresponds to that of shaft 18 and is only slightly less than that of passage 97. Thus, lateral movement of the bayonet 32 is restricted by passage 97.

As will be appreciated, the orientation of the receptacle 68 within handle 14 is dependent upon whether the handle 14 is to be held in a user's left or right hand. In that regard, the position of receptacle 68 determines the orientation of the electrode discharge surface 24, when an electrode 12 is locked in place. For a right-hand electrode assembly 10, the electrode spoon 16 should be substantially aligned with a plane that symmetrically bisects handle body 58 and the discharge surface 24 of spoon 16 should be to the user's left. Alternatively, for a left-hand electrode assembly 10, the spoon's orientation should be reversed, i.e., rotated by 180 degrees, so that the discharge surface 24 of spoon 16 is on the user's right. The requisite alteration in spoon position is accomplished by altering the orientation of the receptacle 68 relative to handle 14 by 180 degrees.

The electrode connection scheme described above has a number of advantages. The bayonet 32 is simple and inexpensive to manufacture and can be machined as part of the end 30 of shaft 18, because its diameter does not exceed that of shaft 18. Further, it is extremely strong, reducing the likelihood of torsional failures experienced with conventional electrode shafts provided with transverse pins that are engaged by the handle.

Finally, the arrangement is simple and reliable, allows the bayonet to be locked in place with a relatively small amount of rotation, and is easily held and used by an operator.

Having described the manner in which the bayonet 32 is connected to the bayonet receptacle 68, the general discussion of the construction and use of electrode assembly 10 will be continued. As described above, the electrode spoon 16, sleeve 20, and a portion of shaft 18 are kept sterile in the unbroken first compartment 54 of package 52 while the bayonet 32 is attached. Because the sleeve 20 will provide a sterile barrier over the handle 30 of shaft 18 and a large portion of handle 14, the user can freely handle these components during assembly without worrying about contaminating them. As a result, the attachment of the electrode 12 to handle 14 is made relatively simple and convenient. Even more importantly, the partially packaged electrode 12 can thus be attached to handle 14 well before it is required, without risking contamination.

With the electrode 12 attached to handle 14, the sleeve 20 must still be deployed before the electrode assembly 10 is used. In that regard, the user must don gloves to avoid contaminating the sleeve 20 while the sleeve 20 is pulled over the handle 14, as described in greater detail below. An assistant may be requested to hold the handle 14 to make the remaining steps easier for the gloved person to perform.

Reviewing the deployment of sleeve 20 in greater detail, first the compartment 54 of package 52 is opened, exposing the collapsed sleeve 20 and electrode spoon 16. The gloved user then grasps the connector 48 provided on sleeve 20 and pulls the sleeve 20 up over the remainder of the electrode shaft 18, the entire handle body 58, and the portion of cable 60 extending to connector 62. The sleeve 20 is dimensioned to conform relatively closely to the handle body 58. However, sleeve 20 fits loosely over cable 60, allowing sleeve 20 to be easily pulled up to the connector 62.

In this manner, the disposable internal electrode 12 is used to effectively sterilize the reusable handle 14. Two such electrode assemblies 10 are connected to a defibrillator by their connectors 64. To use the electrode assemblies 10, the gloved operator grasps handle bodies 58, which are covered by sleeves 20, and positions the electrode spoons 16 on the patient's heart. The "dagger-style" configuration of the handles 14 described above allows this to be done quickly, surely, and comfortably by the user. Because the sleeves 20 extend a distance of roughly one meter from the electrode spoons 16, a sterile field is maintained well beyond the immediate area of the patient.

With the electrode spoons 16 appropriately positioned, the user can then administer a defibrillation shock to the patient by pressing the discharge switches 66 on the handle bodies 58. As a result, the desired electrical impulse will be transmitted from the defibrillator, through the cables 60, the components of handle bodies 58, and the electrode spoons 16 to the patient's heart. After use, the electrodes 12 are removed from the reusable handles 14 and discarded. New disposable electrodes 12 can then be attached to the handles 14, in the manner described above, allowing the defibrillator to be immediately placed back into service.

Alternatively, the handle 14 can be used with a reusable electrode identical to electrode 12 with the exception that the barrier sleeve 20 is omitted. As a result, the entire electrode assembly 10 must be sterilized with, for example, steam, to protect the patient. In view of the multiple-layer construction of handle 14, however, the assembly 10 is relatively resistant to the sterilization process.

Figure 9:
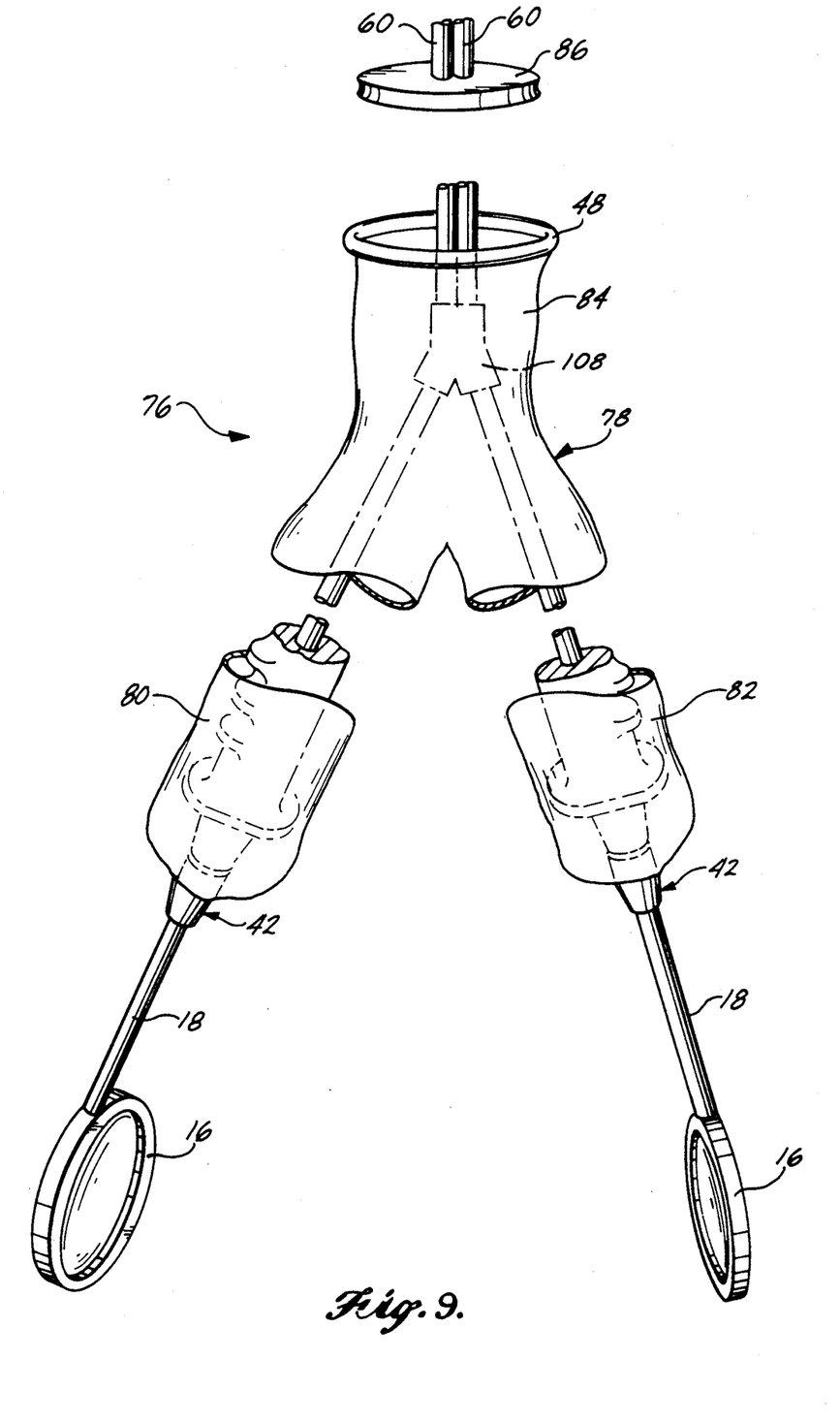
FIG. 9 is an illustration of an alternative embodiment of a pair of disposable electrodes provided as a single unit in accordance with this invention.

Discussing now another embodiment of the internal defibrillation electrode assembly 10, reference is had to FIG. 9. As shown, this embodiment is similar to that discussed above except that now a coupled disposable electrode pair 76 is provided for use with two reusable handles. While the reusable handles are not shown, they are of substantially the same type as the handle 14 described above. In one embodiment, however, the two cables 60 are joined together at the connector end and branch apart at a plastic Y-junction or element 108 before continuing on to the handles 14.

The electrode pair 76 includes a single roughly V-shaped barrier sleeve 78 formed by two substantially tubular elements 80 and 82, joined together at one end to form a common section 84. The dimensions of these tubular elements 80 and 82 roughly approximate those of the sleeve 20 discussed above.

The common section 84 of sleeve 78 ends with a single connector 48, identical to the one employed on each of the sleeves 20 described above. The connector 48 mates with a single connector 86 of the same type as connector 62 described above, except that it encircles both of the defibrillation cables 60. As a result, this design advantageously reduces the number of components required. At the electrode end of each tube 80 and 82, a connector 42, electrode shaft 18, and spoon 16 of the type previously described are connected in the manner described above.

As will be appreciated, the coupled electrode pair 76 may be somewhat less expensive than a pair of electrodes 12 of the type described previously. In that regard, a single connector 48 is now required and packaging requirements may be reduced. Further, because two electrodes are required to perform defibrillation, the coupled electrode pair 76 may offer some convenience over an arrangement in which the electrodes are provided separately.

While a preferred embodiment of the invention has been illustrated and described, it will be appreciated that various changes can be made therein without departing from the spirit and scope of the invention. In that regard, the handle could be used with different styles of electrodes. Further, the barrier sleeve, as well as the entire electrode assembly, could be used in medical applications other than defibrillation. Thus, within the scope of the appended claims, it is to be understood that the invention can be practiced otherwise than as specifically described herein.

The embodiments of the invention in which an exclusive property or privilege is claimed are defined as follows:

1. An electrode for use with a handle to couple a patient to a medical instrument, said electrode comprising:
    electrode means, attachable to the handle, for contacting the patient, and
    barrier means, coupled to said electrode means, being deployed over the handle to provide a barrier between the handle and the patient when the electrode means is attached to the handle.

2. The electrode of claim 1, wherein said electrode means comprises an electrode spoon and a shaft, having first and second ends, said first end of said shaft being attached to said spoon.

3. The electrode of claim 2, wherein said barrier-means comprises a tubular sleeve having first and second ends, said first end of said sleeve being coupled to said shaft.

4. The electrode of claim 3, wherein said tubular sleeve is flexible and deployable between collapsed and extended positions.

5. The electrode of claim 4, further comprising packaging means for receiving said electrode spoon and preventing said electrode spoon from being contaminated.

6. The electrode of claim 5, wherein said packaging means is further for receiving said electrode spoon and said sleeve and comprises a first compartment, for receiving said electrode spoon and said sleeve, and a second compartment for receiving said second end of said shaft.

7. A defibrillation electrode system for use in applying energy from a defibrillator to a patient, said defibrillation electrode system comprising:
   a handle that is coupleable to the defibrillator; and
   an electrode that is coupleable to said handle, said electrode including an electrode element and a sleeve, said electrode element being for contacting the patient, said sleeve being deployable to substantially cover said handle.

8. The electrode system of claim 7, wherein said sleeve includes a pleated main body that allows said sleeve to be easily deployed from a collapsed position to an extended position.

9. The electrode system of claim 7, wherein said sleeve is a substantially tubular piece of latex, roughly three centimeters in diameter and one meter in length.

10. The electrode system of claim 7, wherein said sleeve further comprises electrode connection means for sealably coupling said sleeve to said electrode element and handle connection means for sealably coupling said sleeve to said handle.

11. The electrode system of claim 10, wherein said handle includes a cable and a defibrillator connector, said cable having a first end attached to said handle and a second end attached to said fibrillator connector, said defibrillator connector being for coupling said handle to the fibrillator.

12. The electrode system of claim 11, wherein said electrode element includes a shaft and said cable includes a sleeve connector.

13. The electrode system of claim 12, wherein said electrode connection means comprises a pair of internal and external connectors, provided on one end of said sleeve and attached to said shaft, and wherein said handle connection means comprises a ring-shaped connector provided on the other end of said sleeve for attachment to said sleeve connector.

14. The electrode system of claim 7, wherein said handle further comprises means for engaging said electrode and discharge means for controlling the discharge of energy from the defibrillator to said electrode.

15. An electrode assembly for use with a pair of defibrillator handles, said electrode assembly comprising:
   first and second electrode elements; and
   a tubular barrier sleeve having first, second and third ends, said first and second ends being coupled to said first and second electrode elements.

16. A method of effectively sterilizing a handle for use with a defibrillator, said method comprising the steps of:
   (a) attaching an electrode to said handle, said electrode including a sterile tubular sleeve; and
   (b) extending said sleeve over said handle to provide a sterile barrier between the handle and its environment.

17. An electrode system for use by an operator between a patient and a medical instrument, said electrode system comprising:
   handle means, coupleable to said medical instrument, for being grasped by the operator; and
   electrode means, attachable to said handle means, for contacting the patient and including deployable barrier means for providing a barrier to the transfer of the contaminants between said handle means and the patient.

* * * * *

UNITED STATES PATENT AND TRADEMARK OFFICE
CERTIFICATE OF CORRECTION

PATENT NO. : 5,213,113
DATED : May 25, 1993
INVENTOR(S) : R. L. Hlinsky It is certified that error appears in the above-identified patent and that said Letters Patent is hereby corrected as shown below:

| COLUMN | LINE | |
|---|---|---|
| [57] "Abstract" | 1 | after "electrode" insert --assembly-- |
| 4 | 61 | after "has" insert --a-- |
| 10 (Claim 1 | 61 Line 6) | after "means" insert --for-- |
| 11 (Claim 3 | 1 & 2 Lines 1&2) | "barrier-means" should read --barrier means-- |
| 12 (Claim 11 | 2 Line 6) | "fibrillator" should read --defibrillator-- |

Signed and Sealed this

Eighteenth Day of January, 1994

Attest:

BRUCE LEHMAN

*Attesting Officer*        *Commissioner of Patents and Trademarks*